United States Patent [19]

Brown et al.

[11] 4,315,073

[45] Feb. 9, 1982

[54] TITRATION OF SERUM INFLUENZA ANTIBODY USING PLAQUE REDUCTION NEUTRALIZATION TEST

[75] Inventors: Karen K. Brown, Kansas City, Mo.; Richard C. Stewart, Merriam, Kans.

[73] Assignee: Cutter Laboratories, Inc., Berkeley, Calif.

[21] Appl. No.: 88,684

[22] Filed: Oct. 26, 1979

[51] Int. Cl.³ .................. C12Q 1/70; G01N 33/54
[52] U.S. Cl. .................................. 435/5; 23/230 B; 424/8; 424/12; 424/86; 424/89; 435/7; 435/235
[58] Field of Search .................. 424/8, 12, 86, 89; 23/230 B; 435/5, 7, 235, 236, 238, 239

[56] References Cited

PUBLICATIONS

Tobita, Med. Microbiol. Immunol. (1) vol. 162 pp. 9-14; (2) vol. 162. pp. 23-27 (1975).
Gaush, Applied Microbiol. vol. 16, 1968, pp. 588-594.
Sugiura, Virology, vol. 26, 1965, pp. 478-488.
Lennette et al., Diag. Procd. for Viral & Rickettsial Dis., Amer. Publ. Health Asso. 3rd Ed. 1964, pp. 108-123, 461-469.

Primary Examiner—Anna P. Fagelson
Attorney, Agent, or Firm—James A. Giblin

[57] ABSTRACT

Influenza antibody levels in serum can be measured via plaque reduction neutralization (PRN) technique. Test is more sensitive and specific for measuring anti-infective influenza antibodies than present hemagglutination inhibition (HAI) test and can be used for measuring seronegativity or suceptibility to infection.

25 Claims, 1 Drawing Figure

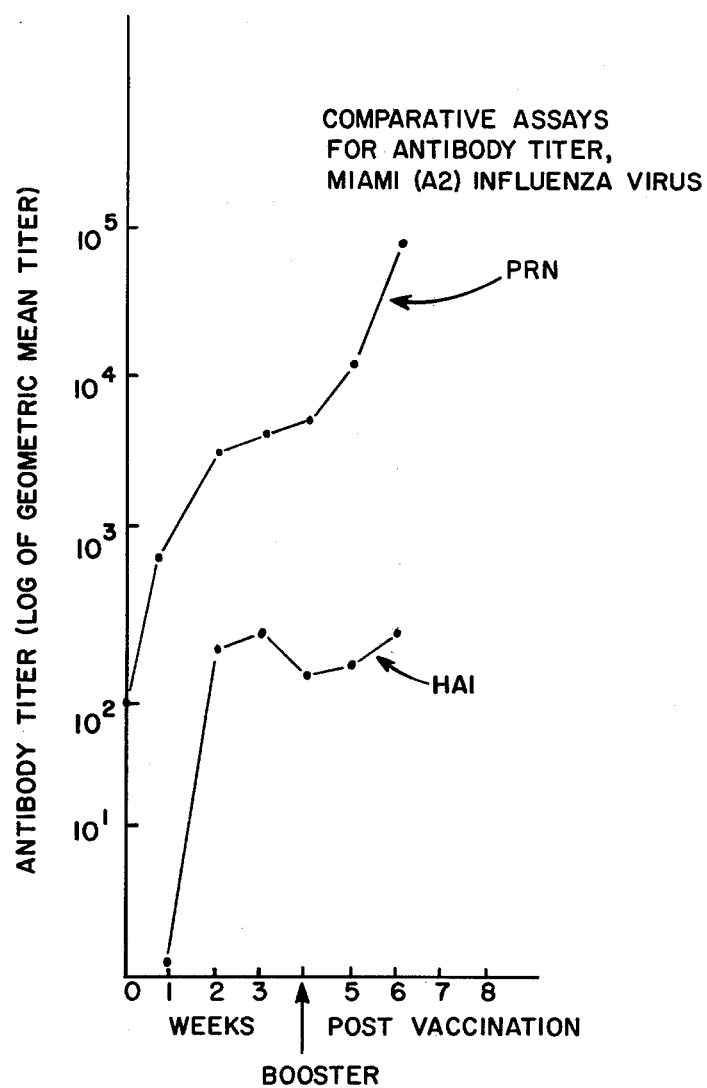

TITRATION OF SERUM INFLUENZA ANTIBODY USING PLAQUE REDUCTION NEUTRALIZATION TEST

RELATED APPLICATION

Patent Application Ser. No. 39,326, filed in our names on May 15, 1979, having common assignee, and entitled, "Influenza Vaccine Production in Liquid Cell Culture". The above application is concerned with the use of a protein hydrolyzing enzyme (such as trypsin) to overcome "one-step growth cycle" of influenza virus in a liquid cell culture, thereby providing a means for avoiding the use of more costly embryonated chicken eggs in the manufacture of influenza vaccines.

BACKGROUND OF THE INVENTION

Field:

This disclosure is concerned generally with a method of determining a serum antibody titer and specifically with using PRN techniques to determine influenza antibody titers in serum samples.

Prior Art:

It is well known that the titer of a given antibody in a blood serum can be determined by taking advantage of the antibody's complexing properties and/or high specificity for its corresponding antigenic substance. Typical techniques for determining serum antibody titers include immunoassays, hemagglutination inhibition (HAI), and plaque reduction neutralization (PRN) methods. PRN techniques are described more fully in, for example, B. D. Davis et al., The Nature of Viruses in Microbiology, pp. 1044–1045, Harper & Row, New York, 1968.

Titration of serum influenza antibody levels is commonly done via HAI technique as introduced by Hirst, G. K., J. Exp. Med. 75:47–64, 1942. The antibody measured is directed to hemagglutinin, a viral surface antigen. A prerequisite for measuring the antibody content of serum involves treatment of the serum with materials such as kaolin or receptor destroying enzyme (RDE) to remove nonspecific inhibitors. The most commonly accepted method of treatment is that of using RDE (see, for example, Measurement of Hemagglutination-Inhibition Antibody to Influenza Virus in the 1976 Influenza Vaccine Program: Methods and Test Reproducibility, Gary R. Nobel, et al., from the World Health Organization Collaborating Center for Influenza Virology Division, and Statistical Activities, Bureau of Laboratories, Center for Disease Control, Atlanta, Georgia in the Journal of Infectious Disease, Vol. 136 Supplement, pp. 5429–5434, December 1977).

Although PRN techniques have been used to determine antibody titers to some other viruses, we are unaware of any prior use of our methodology for the determination or titration of serum influenza antibody levels. We have now found that it is possible to accurately determine serum influenza antibody titers using a PRN technique. Quite surprisingly, the technique results in greater sensitivity and specificity than existing HAI methods and is more useful than HAI methods in determining anti-infective influenza antibodies.

SUMMARY OF THE INVENTION

Our method of titrating a serum sample for influenza antibody level comprises the steps of:

(a) Preparing serial dilutions of the serum to be tested;
(b) reacting each serum dilution with an indicator influenza virus to form separate dilution products;
(c) inoculating separate monolayers of an influenza virus susceptible cell culture with each dilution product;
(d) providing an overlay for the inoculated cultures;
(e) incubating the cultures under conditions sufficient to generate plaque formation;
(f) counting the plaques formed in each culture and relating the counts to a standard to determine the serum antibody titer.

The method disclosed herein can also be used to simply detect the presence of influenza antibody in a serum sample or in screening blood serum samples for influenza antibody seronegativity. The technique can also be used to determine influenza vaccine potency.

In preferred embodiments, the overlay is a semisolid material such as agar and the influenza virus susceptible cell culture is a canine dog kidney cell line of the type described in the publications cited below.

BRIEF DESCRIPTION OF THE FIGURE

The FIGURE is a graph illustrating the greater sensitivity of the PRN technique of this disclosure, as compared with the HAI technique, in determining equine serum influenza antibody levels.

SPECIFIC EMBODIMENTS

The general PRN steps for titrating a given serum antibody are known. The use of plaque assay technique is similar to that described (for example) in articles by K. Tobita et al. in Med. Microbiol. Immunol. 162, 9–14 and 162, 23–27 (1975). The PRN technique can be used to titrate an animal serum (e.g. human, equine, porcine, avian) for antibodies to a variety of influenza viruses. As used herein, the term influenza virus includes any virus capable of causing a febrile disease state in animals (including man) marked by respiratory symptoms, inflammation of mucous membranes and often systemic involvement. These viruses include human, equine, porcine, and avian strains, Types A (A1 and A2) and B.

The cell cultures contemplated as being useful in carrying out the principles of this disclosure include any animal cell line or cell strain capable of being infected by, and which allows the replication and plaque formation of, one or more given influenza virus strains. Although a number of such cells are known and thought to be useful for the techniques disclosed herein, we have had especially good results with an established cell line known as the Cutter Laboratories Dog Kidney (CLDK) cell line. The CLDK cell line has been approved by the U.S. Department of Agriculture for use in producing veterinary vaccines and is similar to the Madin Darby Dog Kidney Cell Line (ATCC No. CCL 34) and to the dog kidney cell line described in U.S. Pat. No. 3,616,203 to A. Brown. A brief history and description of the specific master cell stock used for the cell line of the Examples can be found in our co-pending application Ser. No. 39,326, filed on May 15, 1979, having common assignee, and entitled, "Influenza Vaccine Production in Liquid Cell Culture". It should be understood, however, that the techniques disclosed herein are thought to be useful with any such influenza virus susceptible cell culture.

In the illustrative example below, our PRN technique was used to determine equine serum influenza antibody titers. Knowing such titers is useful for a variety of purposes, including the testing of potency of equine influenza vaccines. The test was found useful in determining the antibody titers of equine A1 and A2 influenza strains.

EXAMPLE I

Titration of Serum Antibody for Equine Influenza Strain A1 or A2 by the Plaque Reduction Neutralization Method The following in vitro test method utilized CLDK cells for the serum assay of Equine Influenza strain A1 or A2 virus.

The CLDK Cells and Growth Medium:

CLDK Cells are prepared as confluent monolayers in 30 ml falcon flasks (3012 or 3013) or 4–6 well culture plates (Costar or Linbro). Cells are grown in MEM Hank's medium with addition of 10 ml/liter 100X non-essential Amino Acids, 10 ml/liter 100X L-Glutamine, and 10% Fetal Calf Serum. The CLDK Cell Growth Media included the following:

CLDK Cell Growth Medium

MEM Hank's Medium
10% Fetal Bovine Serum (Heat Inactivated)
1% 100X Non-Essential Amino Acids
1% 100X L-Glutamine
0.1% 1000X Polymyxin B (30,000 units/ml)
0.1% 1000X Neomycin Sulfate (30,000 mcg/ml)
0.05% 2000X Mycostatin (25 units/ml)
Adjust pH to 6.8 with 1 N HCl Cells should be planted heavily so as to be confluent in 24 hours. A 2 day old cell sheet will not adequately support A1 plaque production but will support A2 plaque production. The cells should be 100% confluent, but not heavy or overgrown, prior to infection.

Solutions:

The solutions used in the PRN technique disclosed herein included the following:

1. 50% Dextrose—50 g Dextrose in 100 cc distilled water, Autoclave 15 minutes 15 lbs. 2. 2% Purified Agar (Difco)—20 g in 1000 cc distilled water, Autoclave 15 minutes 15 lbs.
3. 0.1% Trypsin Solution—0.1 g Trypsin (1:250) in 100 cc sterile 0.01M PBS, filter sterilize.
4. PBS—Stock—27.4 g anhydrous $Na_2HPO_4$ + 114 g $NaH_2PO_4$—$H_2O$ in distilled $H_2O$. Q.S. to 1000 cc.
5. 1.0% DEAE Dextran—1.0 g DEAE Dextran in 100 cc sterile distilled water, filter sterilize.
6. 10% $NaHCO_3$—10.0 g $NaHCO_3$ in 100 cc sterile distilled water, filter sterilize.
7. 0.01M PBS—40 cc PBS—Stock + 8.5 g NaCl in distilled $H_2O$. Q.S. 1000 cc. Filter sterilize through a 0.2$\mu$ filter. Adjust pH to 7.16–7.20 with either 1 N HCl or 1 N NaOH.
8. 2.5 M Hepes buffer—30 g/50 cc of distilled water.

Serum Dilutions and Virus Challenge

1. Two to ten-fold serial dilutions are made of the serum to be assayed (0.1 + 0.9). Dilutions are made in the complete influenza medium (described below) plus 10.0 cc/liter of 2.5 M Hepes Buffer.

Complete Influenza Medium—ingredients/liter of MEM Hank's

|  | Basal Media |
|---|---|
| Gibco MEM Vitamins | 30 cc |
| 100X Non-Essential Amino Acids | 10 cc |

-continued

|  | Basal Media |
|---|---|
| 100X L-Glutamine | 10 cc |
| 1000X Polymyxin B | 1 cc |
| 1000X Neomycin Sulfate | 1 cc |
| 2000X Mycostatin (500,000 u/10 cc) | .5 cc |
| 50% Dextrose | 2.6 cc |

Q.S. to 1000 cc with MEM Hank's Medium pH to 6.8 using a 10% Sodium Bicarbonate Solution 2. The number of dilutions used depends on the serum being assayed. When screening seronegative animals, dilutions from $10^{-1}$ to $10^{-3}$ are used. After vaccination, dilutions from $10^{-1}$ to $10^{-8}$ may be required.

3. After dilutions are made, 0.2 cc from each dilution is transferred to clean tubes for virus challenge.

4. Dilutions may be made ahead in capped tubes and frozen at $-20°$ C. until used.

5. On the test day, 0.2 cc aliquots of dilutions are thawed and the indicator virus is diluted using the complete infuenza medium plus 10.0 cc/liter of 2.5 M Hepes Buffer without Fetal Calf Serum. The influenza strain is diluted to the point where 60–160 plaque forming units are produced per 0.1 cc.

6. 0.2 cc of the diluted indicator virus is added to an equal volume of each dilution (0.2 cc) of serum and mixed well.

7. Equal volumes of indicator virus dilution and diluent (complete influenza medium plus 10.0 cc/liter of 2.5 M Hepes Buffer) are combined in a separate tube as a virus control.

8. All virus challenged tubes are incubated at room temperature for one hour. Racks of tubes containing the serum-virus mixtures are shaken at least once during this incubation period.

9. At the end of the above incubation period, the CLDK cells are prepared for infection by the serum virus mixtures by pouring off the liquid medium over the confluent CLDK monolayers. Flasks are placed no more than 4 high on a level surface—preferably around the edge of a table. Plates are set individually around the table.

10. Two CLDK monolayer flasks or 2 wells of a plate are then inoculated with 0.1 cc from each virus-serum dilution tube (from C.6.) using a BBL Fibrometer gun. Inoculum should be directed toward the center of flasks or wells. Flasks or plates should not be picked up or moved during inoculation or overlay.

11. At the beginning, middle and end of the test, control flasks or wells are inoculated with 0.1 cc of the 1:1 virus-diluent mixture (7).

12. After flasks are inoculated, caps or lids are replaced without moving flasks or plates.

13. Inoculated flasks or plates are incubated closed at room temperature 1–2 hours to allow for virus adsorption.

14. At the end of the incubation period caps are removed from the flasks or lids from plates, without moving the flasks or plates, and each flask or well is overlayed with 7.5 to 8.0 cc of the following flu overlay medium:

Semi-Solid Overlay Preparation

The overlay is prepared as follows:

A. Determine total volume of overlay needed at 8.0 cc/flask or 5.0 cc/well in plates.

-continued

B. Total Volume × 0.0026 = Amt. 50% Dextrose
   Total Volume × 0.03 = Amt. MEM Vitamins
   Total Volume × 0.01 = Amt. 100X Non-Essential Amino Acids
   Total Volume × 0.01 = Amt. 100X L-Glutamine
   Total Volume × 0.30 = Amt. 2% Purified Agar (Difco)
   Total Volume × 0.10 = Amt. 10X MEM Hank's Medium without Bicarbonate
   Total Volume × 0.015 for A1 = Amt. 0.1% Trypsin Solution (1:250 Filter Sterilized)
   Total Volume × 0.010 for A2 = Amt. 0.1% Trypsin Solution (1:250 Filter Sterilized)
   Total Volume × 0.01 = Amt. 1% DEAE Dextran
   Total Volume × 0.005 = Amt. 10% $NaHCO_3$
   Total Volume × 0.001 = Amt. 1000X Polymyxin B
   Total Volume × 0.001 = Amt. 1000X Neomycin Sulfate
   Total Volume × 0.0005 = Amt. 2000X Mycostatin
C. Q.S. to Total Volume with Sterile Distilled Water.
D. Adjust pH to 6.8 with 1 N HCl.
   Using a 10.0 cc continuous pipetting Cornwall syringe and a 14 gauge 1½ inch needle, the agar is ejected at the top of the flask (opposite the cell sheet) or against the side of wells while the flasks or plates remain on the table.

15. When the agar overlay has solidified (15–20 minutes) the flasks or plates are inverted, stacked no more than 4 high, and placed at 34° C.–37° C. for 2–5 days. Plaques are easily observed as round cloudy areas. One plaque type is generally found. Plates must be incubated in $CO_2$ atmosphere.

16. At the end of the plaque development period the plaques are counted. The plaques may be counted directly or 2.0 cc of a crystal violet-alcohol stain can be applied to the agar and allowed to remain from 4 to 24 hours. After this staining period the agar and stain are washed off with tap water. Using this method an automatic counter may be used.

17. Known techniques such as Linear Regression or Reed Muench methods are used to analyze the plaque results.

Comparison with HAI Method

The greater sensitivity of our PRN technique was observed when we compared our technique with conventional HAI titration for serum levels of antibody to the A2 Equine influenza Virus (Miami strain). The greater sensitivity was found for not only unextracted serum samples but also sera treated with varying amounts of kaolin and with RDE. The observed HAI and our PRN titers are shown in Tables I and II, respectively.

TABLE I

A2 (Miami) HAI Titers (Reciprocal) of Horse Sera Before and After Extraction with Various Amounts of Kaolin or RDE

| Horse | Unextracted | TREATMENT OF SERA | | | |
| --- | --- | --- | --- | --- | --- |
| | | 1.2% Kaolin | 6% Kaolin | 12% Kaolin | RDE |
| 324 | 320 | 160 | 40 | 40 | 40 |
| 325 | 640 | 320 | 160 | 160 | 160 |
| 326 | 320 | 320 | 160 | 80 | 160 |
| 327 | 640 | 320 | 160 | 80 | 160 |
| 330 | 640 | 320 | 80 | 40 | 80 |
| 334 | 320 | 320 | 160 | 80 | 80 |
| 337 | 1280 | 1280 | 640 | 320 | 320 |
| 338 | 640 | 320 | 320 | 160 | 160 |
| 339 | 80 | 160 | 40 | 40 | 40 |
| 340 | 640 | 640 | 160 | 160 | 320 |
| Geo. Mean Titer | 453 | 343 | 139 | 92 | 121 |

TABLE I-continued

A2 (Miami) HAI Titers (Reciprocal) of Horse Sera Before and After Extraction with Various Amounts of Kaolin or RDE

| Horse | Unextracted | TREATMENT OF SERA | | | |
| --- | --- | --- | --- | --- | --- |
| | | 1.2% Kaolin | 6% Kaolin | 12% Kaolin | RDE |
| % Reduction in Titer | — | 24 | 69 | 80 | 73 |

Treatment of the serum with increasing amounts of kaolin reduced the level of HAI antibodies to the hemagglutinin antigen as much as 80 percent and RDE treatment reduced the antibody level about 70 percent.

TABLE II

A2 (Miami) PRN Titers of Horse Sera Before and After Extraction with Various Amounts of Kaolin or RDE

| Horse | Unextracted | TREATMENT OF SERA | | | |
| --- | --- | --- | --- | --- | --- |
| | | 1.2% Kaolin | 6% Kaolin | 12% Kaolin | RDE |
| 324 | 6753 | 5672 | 5703 | 9026 | 5365 |
| 325 | 11276 | 7033 | 12053 | 13572 | 15714 |
| 326 | 4259 | 8656 | 5921 | 8363 | 12270 |
| 327 | 11008 | 11876 | 19819 | 8562 | 15453 |
| 330 | 5951 | 12656 | 9716 | 7146 | 12133 |
| 334 | 6415 | 6234 | 6817 | 6372 | 15898 |
| 337 | 36000 | 36757 | 38080 | 42657 | 23385 |
| 338 | 10308 | 4377 | 13722 | 7838 | 9535 |
| 339 | 7322 | 2035 | 4007 | 4312 | 6776 |
| 340 | 11493 | 15765 | 15429 | 15409 | 8865 |
| Geo. Mean Titer | 9181 | 8361 | 10561 | 9887 | 11521 |
| % Reduction in Titer | 0 | 9 | 0 | 0 | 0 |

Neutralization of viral infectivity, as demonstrated by antibody inhibition of viral cytopathology was unaffected by the serum treatment methods when the PRN technique was used for determination of antibody levels.

EXAMPLE 2

Sixteen horses were vaccinated with a killed virus vaccine containing the A2 Equine Influenza Virus (Miami Strain) and were boostered at 4 weeks after the first injection. The resulting antibody levels of each horse were assayed weekly for 6 weeks using the HAI and PRN methods of determination. A comparison of the antibody levels obtained is shown in the FIGURE.

HAI antibody titers reached a level of about 170 and remained on a plateau even after the booster injection, while the PRN titers continued to rise and show an anemnestic response after the booster injection.

EXAMPLE 3

The greater sensitivity of our PRN technique was again observed when we compared our technique with the HAI titration for detection of serum antibodies to the A2 Equine Influenza Virus in horses for the determination of seronegativity or susceptibility to infection. Sera from 35 horses showing an HAI antibody titer of less than 1:8 (the lowest limit of assay) were tested by our PRN technique. A comparison of the titers is shown in Table III.

TABLE III

PRN Antibody Titers of HAI Seronegative Horses (A2 Strain)

| Horse | HAI Titer | PRN Titer |
| --- | --- | --- |
| 125 | <8 | 0 |

TABLE III-continued

| PRN Antibody Titers of HAI Seronegative Horses (A2 Strain) | | |
|---|---|---|
| Horse | HAI Titer | PRN Titer |
| 126 | <8 | 0 |
| 19 | <8 | 0 |
| 2 | <8 | 1 |
| 61 | <8 | 1 |
| 48 | <8 | 1 |
| 11 | <8 | 1 |
| 21 | <8 | 3 |
| 17 | <8 | 4 |
| 69 | <8 | 4 |
| 79 | <8 | 5 |
| 13 | <8 | 6 |
| 54 | <8 | 8 |
| 38 | <8 | 9 |
| 23 | <8 | 9 |
| 128 | <8 | 9 |
| 55 | <8 | 10 |
| 29 | <8 | 11 |
| 73 | <8 | 12 |
| 129 | <8 | 14 |
| 40 | <8 | 15 |
| 53 | <8 | 18 |
| 20 | <8 | 34 |
| 37 | <8 | 37 |
| 89 | <8 | 61 |
| 18 | <8 | 96 |
| 68 | <8 | 97 |
| 131 | <8 | 104 |
| 130 | <8 | 104 |
| 121 | <8 | 141 |
| 4 | <8 | 155 |
| 16 | <8 | 391 |
| 32 | <8 | 566 |
| 52 | <8 | 874 |
| 31 | <8 | 1021 |

PRN antibody titers of sera from horses determined to be seronegative (<1.8) by the HAI method can range from levels of 0 to 1021.

It is thought that our above-disclosed PRN techniques could be used for determining influenza vaccine potency. The vaccine potency testing would comprise the steps of:

(a) vaccinating and boostering an influenza susceptible seronegative animal with an influenza test vaccine under conditions sufficient (e.g. dose, time schedule, etc.) to stimulate antibody production;

(b) bleeding the animal at a given time after vaccination or booster and obtaining a blood serum sample;

(c) testing the serum sample by the PRN technique of this disclosure to determine the level of antibody stimulation by the test vaccine; and (d) comparing the level of influenza antibody stimulation with a known acceptable level (or standard), thereby determining the potency of the test vaccine.

In view of the above disclosures, it is thought that numerous variations will occur to those skilled in the art. Accordingly, it is intended that the above examples should be construed as illustrative only and that the scope of this invention should be limited only by the following claims.

We claim:

1. A method of determining the titer of anti-infective antibodies to influenza virus in a blood serum sample, the method comprising the steps of:

(a) preparing serial dilutions of the serum sample;

(b) reacting each dilution with an indicator infuenza virus to form separate dilution products;

(c) inoculating separate influenza virus susceptible monolayer cell cultures with the separate dilution products;

(d) providing an overlay for the inoculated cultures;

(e) incubating the cultures in the presence of a protein hydrolyzing enzyme under conditions sufficient to allow plaque formation;

(f) counting the plaques in each culture and relating the counts to a standard to determine the antibody titer.

2. The method, as claimed in claim 1, wherein the serum sample is a human, equine, porcine or avian serum.

3. The method of claim 1 wherein the indicator influenza virus is selected from the influenza A and influenza B strains.

4. The method of claim 1 wherein each dilution of step (b) is reacted with substantially equal amounts of the indicator virus.

5. The method of claim 1 wherein the overlay of step (d) is a semi-solid material.

6. The method of claim 5 wherein the overlay material is agar.

7. The method of claim 1 wherein the serum sample is an equine serum.

8. The method of claim 7 wherein the indicator influenza virus is selected from influenza A1 and influenza A2 strains.

9. The method of claim 1 wherein the protein hydrolyzing enzyme of step (e) is trypsin.

10. A screening test to determine seronegativity for anti-infective influenza antibodies in a blood serum sample, the method comprising the steps of:

(a) reacting the serum sample with an indicator influenza virus to form a reaction product;

(b) inoculating an influenza virus susceptible monolayer cell culture with the product of step (a);

(c) providing an overlay for the inoculated culture;

(d) incubating the culture in the presence of a protein hydrolyzing enzyme under conditions sufficient to allow plaque formation; and (e) counting any plaques so formed and relating the counts to a standard to determine seronegativity of the serum sample.

11. The method of claim 10 wherein the serum sample is a human, equine, porcine or avian serum.

12. The method of claim 10 wherein the influenza virus is selected from the influenza A and influenza B strains.

13. The method of claim 10 wherein the overlay of step (c) is a semi-solid material.

14. The method of claim 13 wherein the overlay material is agar.

15. The method of claim 10 wherein the serum sample is an equine serum.

16. The method of claim 15 wherein the indicator virus is selected from influenza A1 and influenza A2 strains.

17. The method of claim 10 wherein the protein hydrolyzing enzyme of step (d) is trypsin.

18. A method of detecting the presence of anti-infective influenza antibody in a blood serum sample, the method comprising the steps of:

(a) reacting the serum sample with an indicator influenza virus to form a reaction product;

(b) inoculating an influenza virus susceptible confluent cell culture with the reaction product of step (a);

(c) providing an overlay for the inoculate of step (b);

(d) incubating the inoculate in the presence of a protein hydrolyzing enzyme under conditions sufficient to allow plaque formation;

(e) examining the incubated product of step (d) and relating the examination to a standard to determine the presence of influenza antibody in the serum sample.

19. The method of claim 18 wherein the serum sample is a human, equine, porcine, or avian serum.

20. The method of claim 18 wherein the indicator influenza virus is selected from the influenza A and influenza B strains.

21. The method of claim 18 wherein the overlay of step (c) is a semi-solid material.

22. The method of claim 21 wherein the overlay is agar.

23. The method of claim 21 wherein the serum sample is an equine serum.

24. The method of claim 23 wherein the indicator influenza virus is selected from influenza A1 and influenza A2 strains.

25. The method of claim 18 wherein the protein hydrolyzing enzyme of step (d) is trypsin.

* * * * *